United States Patent

Salka et al.

[11] Patent Number: 5,578,642
[45] Date of Patent: Nov. 26, 1996

[54] SELF-EMULSIFYING AND/OR EMOLLIENT AGENTS

[75] Inventors: Barry A. Salka, Fair Lawn; Bruce W. Gesslein, Brick, both of N.J.; Norman Milstein, Montgomery, Ohio

[73] Assignee: Henkel Corporation, Plymouth Meeting, Pa.

[21] Appl. No.: 292,115

[22] Filed: Aug. 17, 1994

[51] Int. Cl.$^6$ .......................... A61K 31/225; A61K 7/42; C11D 3/20; B01J 13/00
[52] U.S. Cl. .......................... 514/547; 252/312; 424/59; 424/70.22; 514/873; 510/434
[58] Field of Search ...................... 252/309, 312, 252/314, 174.25, DIG. 5, 173; 424/59, 70.31, 70.22; 560/190, 201, 204; 514/547, 873

[56] References Cited

U.S. PATENT DOCUMENTS

| | | | |
|---|---|---|---|
| 2,528,378 | 10/1950 | Mannheimer | 548/352.1 |
| 2,781,354 | 2/1957 | Mannheimer | 548/352.1 |
| 3,692,822 | 9/1972 | Hay et al. | 560/98 |
| 3,943,234 | 3/1976 | Roggenkamp | 252/DIG. 5 |
| 3,964,500 | 6/1976 | Drakoff | 132/202 |
| 4,425,458 | 1/1984 | Linder et al. | 524/314 |
| 4,940,574 | 7/1990 | Kaplan | 424/59 |
| 5,286,397 | 2/1994 | Schmid et al. | 252/565 |
| 5,434,237 | 7/1995 | Weinelt et al. | 528/272 |

FOREIGN PATENT DOCUMENTS

| | | |
|---|---|---|
| 2092360 | 3/1993 | Canada. |
| 63-17042-B | 4/1988 | Japan. |
| WO91/3531 | 3/1991 | WIPO. |

OTHER PUBLICATIONS

Derwent Abstract, AN–91–074449/11 (Mar. 1991).
Derwent Abstract, AN–80–24318C/14 (Apr. 1980).

*Primary Examiner*—Richard D. Lovering
*Assistant Examiner*—Daniel S. Metzmaier
*Attorney, Agent, or Firm*—Ernest G. Szoke; Wayne C. Jaeschke; Steven J. Trzaska

[57] ABSTRACT

There is provided a composition and process for preparing self-emulsifying or emollient agents comprising reacting from about 1 mole of azelaic acid with from about 1 to about 1.25 moles of a C12–18 fatty alcohol to form an azelaic acid monoester having the general formula I–IV:

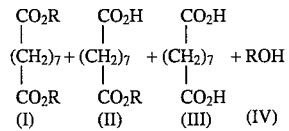

wherein R is a C12–18 fatty alcohol, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of said self-emulsifying or emollient agent.

22 Claims, No Drawings

SELF-EMULSIFYING AND/OR EMOLLIENT AGENTS

FIELD OF THE INVENTION

The present invention generally relates to monoazeleic esters. More particularly, there is provided a composition and process for making self-emulsifying or emollient agents by esterifying one of the carboxylic acid functions of azelaic acid.

BACKGROUND OF THE INVENTION

An emulsion is a mixture of two or more immiscible liquids, one being present in the other in the form of droplets. In the classic emulsion, the oil may either be dispersed in the water (oil-in-water or o/w emulsion) or the water dispersed in the oil (water-in-oil, w/o, or inverse emulsion). This terminology is important because of the external phase, a key factor in emulsion formulation and design.

In emulsion formulation, the goal is to achieve the best combination of emulsion properties to fulfill the application needs and stability requirements. The key or active ingredients may or may not be the major ingredient. The main ingredient is most frequently the continuous phase and this dictates the type of emulsion, o/w or w/o. For economic as well as technical reasons, most commercial emulsions are oil-in-water and have low oil (internal) phase levels.

The use of the least amount of emulsifier is possible when a choice is made that most nearly matches the requirements for ionic type, HLB (hydrophile-lipophile balance), and the emulsifier chemical type.

The choice of ionic type: anionic, cationic, amphoteric or nonionic, will influence many properties of the final emulsion. The HLB is an expression of the relative simultaneous attraction of an emulsifier for water and oil (or for the two phases of the emulsion system being considered). It is determined by the chemical composition and the extent of ionization of the emulsifier. For example, ionic emulsifiers change HLB values radically with change in pH and/or salt content of the formula whereas nonionic emulsifiers exhibit a more constant HLB under these circumstances.

Emulsions are used in a variety of fields such as textiles, leather and metal treatment; foods, cosmetics, pharmaceuticals and paints; in agricultural chemicals, polymerizations, cleaning and polishing; and ore and petroleum recovery. In the personal care field which includes products such as cleansing bars and shampoos, cold creams, after-shaves, anti-perspirants, lotions and moisturizers, and pharmaceutical ointments, just to name a few, emulsifiers are added to both emulsify and thicken these compositions.

Emollients is the name given to a class of chemicals which are used in topical personal care preparations such as facial cleaners, handcreams and the like, to exert a softening and protective effect upon skin tissue. Mineral oil is widely used in personal care products as an emollient because of its low cost. However, mineral oil has an undesirable oily feel which is carried over into the finished product. There thus exists a need for compounds which will reduce the oily feel of mineral oil without reducing its emolliency. Moreover, typical personal care preparation utilize both an emulsifier for thickening and emulsifying the preparation and an emollient for providing good skin-feel if the product is intended to come into contact with skin. The use of two separate components to achieve the desired result is, as expected, more expensive and adds to the production costs of the products. Thus, a primary object of the present invention is to provide a compound which has both emulsifying and/or emolliency imparting properties.

SUMMARY OF THE INVENTION

Other than in the operating examples, or where otherwise indicated, all numbers expressing quantities of ingredients or reaction conditions used herein are to be understood as modified in all instances by the term "about".

It has now been surprisingly found that by esterifying only one of the carboxylic acid functions of azelaic acid, an azelaic acid monoester is formed which acts as a self-emulsifier and/or emollient, imparting both exceptional emulsifying or skin-feel benefits when incorporated into personal care products.

In accordance with the present invention, there is provided a process for preparing self-emulsifying or emollient agents comprising reacting from about 36 to about 50 weight percent of azelaic acid with from about 50 to about 64 weight percent of a C12-18 fatty alcohol to form a self-emulsifying or emollient agent comprised of compounds having the general formula I–IV:

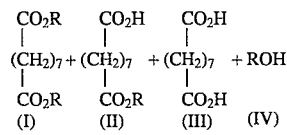

wherein R is a C-12 tp C-18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of the agent.

The self-emulsifying or emollient agents formed according to this process possess exceptional emulsifying and emolliency characteristics when used in compositions, such as personal care products, which require such properties. Thus, in accordance with the present invention, there is also provided an aqueous composition comprising water and a self-emulsifying or emollient agent comprised of compounds having the general formula I–IV:

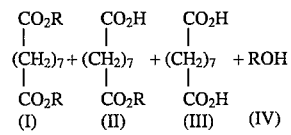

wherein R is C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of the agent.

In a particularly preferred embodiment, the aqueous composition contains from about 20 to about 80 weight percent water, from about 1 to about 25 weight percent self-emulsifying or emollient agent, and from about 0.1 to about 20 weight percent of at least one active ingredient, all weight being based on the weight of the aqueous composition.

In yet another embodiment of the present invention there is provided a method of emulsifying or imparting emolliency to an aqueous composition comprising adding an effective amount of a self-emulsifying or emollient agent comprised of compounds having the general formula I–IV:

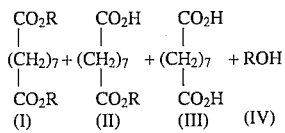

wherein R is a C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of the agent.

In a final aspect of the invention, there is provided a composition comprising compounds of the general formula I–IV:

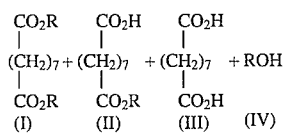

wherein R is a C12–18 alkyl group, and the composition contains from about 40 to about 50 weight percent of (I), from about 50 to about 60 weight percent of (II), from about 1 to about 2 weight percent of (III), and from about 0 to about 1 weight percent of (IV), all weights being based on the weight of the composition.

DETAILED DESCRIPTION OF THE INVENTION

The self-emulsifying or emollient agents of the present invention contain, as their principal surface active components, azelaic acid monoesters, formed by the partial or half esterification of azelaic acid with a fatty alcohol. Neutralization of the azelaic acid monoester results in the formation of an emulsifier. Because the azelaic acid monoester is comprised of a hydrophilic portion and a hydrophobic portion, it can thus function as a self-emulsifier. These azelaic acid monoesters also exhibit emollient characteristics. Thus, when used in personal care preparations, they exhibit exceptional aesthetic emollient properties and can therefore be used as self-emulsifying emollients. The improved emollient or skin feel of these monoesters enables formulation chemists to produce products that out-perform similar products in aesthetic feel.

The main surface active components of the self-emulsifying/emollient agents of the present invention are monoesters of azelaic acid. The monoesters are formed by reacting azelaic acid with a C12–18 fatty alcohol, in the presence of a catalyst. According to one embodiment of the present invention, the self-emulsifying and/or emollient agents are comprised of compounds having the general formula I–IV:

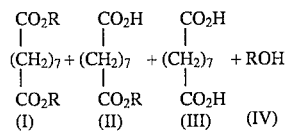

wherein R is a C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of the agent.

The self-emulsifying and/or emollient agents are formed by reacting from about 36 to about 50, and preferably about 40 weight percent of azelaic acid, with from about 50 to about 64, and preferably about 60 weight percent of a C12–18 fatty alcohol, all weights being based on the weight of the agent. Particularly preferred fatty alcohols are the C12–18 Guerbet alcohols.

Catalysts suitable for this reaction are well-known in the art and include, for example, inorganic alkalis such as alkali metal oxides and hydroxides, e.g., potassium hydroxide, protic and Lewis acids, e.g., boron trifluoride, stannic chloride and sulfuric acid. Amines, quaternary ammonium compounds, and other acids may also be employed. Mixtures of catalysts may also be employed. Certain reactive substrates known in the art may eliminate the need for such catalysts.

Preferably, an acidic catalyst is used in this reaction in an amount of from about 0.10 to about 0.25 weight percent, based on the weight of the alcohol. Most preferably, from about 0.15 to about 0.2 weight percent of p-toluenesulfonic acid (p-TSA) is used as the catalyst in the reaction, along with 0.18% hypphosphorous acid, 50% as a color inhibitor.

The azelaic acid component of the present invention may be obtained via any number of methods. One method involves the ozone oxidation of oleic acid. According to this method, oleic acid is oxidized using ozone to form azelaic acid and pelargonic acid. The preparation of azelaic acid is disclosed in U.S. Pat. No. 2,813,113, the entire contents of which are incorporated herein by reference. The azelaic acid produced is di-basic and has a melting point of about 102° C.

In one particularly preferred embodiment, from about 39 to about 44, and preferably from about 41 to about 42 weight percent of azelaic acid is reacted with from about 56 to about 61, and preferably from about 58 to about 59 weight percent of isocetyl alcohol, all weights being based on the weight of the agent, in the presence of from about 0.15 to about 0.2% by weight, based on the weight of the alcohol, of a p-TSA catalyst, to form an isocetyl azelate having both self-emulsifying and/or emollient characteristics. The azelaic acid monoester formed preferably has an HLB in the range of 2 to 13; approximately 2 unneutralized and approximately 13 neutralized.

The present invention also provides an aqueous composition containing the disclosed self-emulsifying and/or emollient agents, in combination with water. According to this aspect of the invention, from about 1 to about 25, and preferably from about 5 to about 10 weight percent, based on the weight of the aqueous composition, of a self-emulsifying and/or emollient agent comprised of compounds having the general formula I–IV:

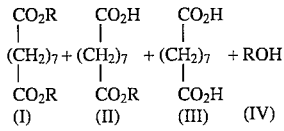

wherein R is a C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of the agent, is contained in an aqueous composition, with the remainder being water, for the purpose of imparting emulsifying and/or emolliency characteristics to the aqueous composition. In a particularly preferred embodiment of the invention, the self-emulsifying and/or emollient agent is isocetyl azelate. The isocetyl azelate is formed by reacting from about 39 to about 44, and preferably about 42 weight percent of azelaic acid with from about 56 to about 61, and preferably about 58 weight percent of isocetyl alcohol, all weights being based on the weight of the agent. This reaction is conducted in the presence of from about 0.15 to about 0.20 weight percent, based on the weight of the alcohol, of a catalyst consisting of sulfonic acids and 0.18% hypophosphorous, 50% of which acts as color inhibitor.

The aqueous composition will preferably include the self-emulsifying and/or emollient agent of the present invention along with from about 0.1 to about 25 weight percent, based on the weight of the aqueous composition, of at least one active ingredient, with the balance being water. Additional emulsifying or emollient agents may also be optionally employed.

Suitable active ingredients which may be employed include, but are not limited to, sunscreen, moisturizers, detergents, thickening agents, emulsifiers, conditioning agents and the like. The detergents may include a variety of surfactants of the anionic type, nonionic type, amphoteric type and mixtures thereof.

Suitable anionic detergents include sodium lauryl sulfate, sodium oleyl succinate, ammonium lauryl sulfosuccinate, sodium lauryl ether sulfate, ammonium lauryl sulfate, sodium dodecylbenzene sulfonate, triethanolamine dodecylbenzene sulfonate, sodium N-lauryl sarcosinate, sodium laureth sulfate and triethanolamine lauryl sulfate. Suitable amphoteric or ampholytic detergents include N-lauryl-N'carboxymethyl-N-(2-hydroxyethyl) ethylenediamine, cocobetaine, the Miranol compounds in U.S. Pat. Nos. 2,528,378 and 2,781,354, cocoamidopropyl hydroxysultaine, lauroampho diacetate and cocoamidopropyl betaine. Other suitable amphoteric detergents include the quaternary cycloimidates, betaines and sultaines disclosed in U.S. Pat. No. 3,964,500. Nonionic surfactants include polysorbate 20, laurylamide DEA and sucrose monococate.

The aqueous composition of the present invention, in addition to containing the self-emulsifying and/or emollient agent of the present invention, at least one active ingredient, water and optional second emulsifying or emollient agents, may also include coloring agents, fragrances, proteins, humectants, salts, preservatives, essential oils and the like.

The aqueous composition of the present invention is formulated utilizing techniques that are well-known in the art. Typically, the components are combined with mixing and the addition of heat if necessary until a uniform, homogeneous product is formed. The water-soluble and water-insoluble ingredients are mixed together separately and are combined with the self-emulsifying and/or emollient producing azelaic acid monoester of the present invention to form emulsions.

In yet another aspect of the present invention, there is disclosed a method of emulsifying and/or imparting emolliency to an aqueous composition comprising adding an effective amount of a self-emulsifying and/or emollient agent comprised of compounds having the general formula I–IV:

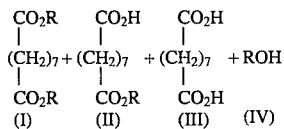

wherein R is a C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of the agent, formed by reacting azelaic acid with a C12–18 fatty alcohol.

When using the self-emulsifying and/or emollient agent of the present invention to emulsify and/or provide emolliency properties to an aqueous composition, from about 1 to about 25, and preferably from about 5 to about 10 weight percent, based on the weight of the aqueous composition, of the self-emulsifying and/or emollient agent should be added. In a particularly preferred embodiment of the present invention, the self-emulsifying and/or emollient agent is the azelaic acid monoester, and particularly, isocetyl azelate. The isocetyl azelate is formed by reacting from about 39 to about 44, and preferably from about 41 to about 42 weight percent of azelaic acid with from about 56 to about 61, and preferably from about 58 to about 59 weight percent of isocetyl alcohol, all weights being based on the weight of the agent. This reaction is conducted in the presence of from about 0.15 to about 0.20 weight percent, based on the weight of the alcohol, of a catalyst along with about 0.18% hypophosphorous acid, 50% of which acts as a color inhibitor. Preferably, the catalyst used is a sulfonic acid. Examples of aqueous compositions to which an effective amount of the self-emulsifying and/or emollient agent can be added include, but are not limited to, sunscreen lotions, skin softening lotion, detergents, thickening compositions, conditioning lotions, and the like.

The present invention also provides a composition comprised of compounds having the general formula I–IV:

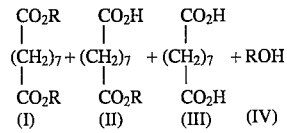

wherein R is a C12–18 alkyl group, and the composition contains from about 40 to about 50 weight percent of (I), from about 50 to about 60 weight percent of (II), from about 1 to about 2 weight percent of (III), and from about 0 to about 1 weight percent of (IV), all weights being based on the weight of the composition.

The composition is formed by reacting from about 36 to about 50, and preferably about 42 weight percent of azelaic acid, with from about 50 to about 64, and preferably about 58 weight percent of a C12–18 fatty alcohol, all weights being based on the weight of the agent. Particularly preferred fatty alcohols are the C12–18 Guerbet alcohols.

In one particularly preferred embodiment, from about 39 to about 44, and preferably from about 41 to about 42 weight percent of azelaic acid is reacted with from about 56 to about 61, and preferably from about 58 to about 59 weight percent of isocetyl alcohol, all weights being based on the weight of the agent, in the presence of from about 0.15 to about 0.20% by weight, based on the weight of the alcohol, of a p-TSA catalyst and 0.18% hypophosphorous acid, 50% of which acts a color inhibitor, to form a composition whose primary surface active component is isocetyl azelate having both self-emulsifying and/or emollient characteristics. The composition formed preferably has an HLB in the range of 2 to 13; approximately 2 unneutralized and approximately 13 neutralized.

The following examples set forth herein below are illustrative of the present invention and will be useful to one of ordinary skill in the art in practicing the invention. However, the invention should be in no way limited by these examples. Also, unless otherwise indicated, all percentages are by weight.

EXAMPLES

EXAMPLE 1

Preparation of Isocetyl Azelate

RAW MATERIALS

| | |
|---|---|
| Isocetyl Alcohol (Eutanol G-16) | 57.9% |
| Azelaic acid (Emerox 1144) | 41.9% |
| Hypophosphorous Acid, 50% | 0.1% |
| p-Toluenesulfonic Acid | 0.1% |

PROCEDURE

1. Charge the raw materials in the order listed above with agitation and nitrogen sparge.
2. Begin heating to 160° C. Water will begin to distill at 120° C.
3. Continue heating at 160° C. until the distillation of water is complete.
4. Sample each hour until the acid number is stable within 1.0 unit on two consecutive samples.
5. Cool to 100° C. and extract four times with 40% of the batch weight of hot water at 95° C.
6. Separate layers.
7. Dry the upper layer at 105° C. and 27 inches vacuum with nitrogen sparge.
8. Cool to 20° C. and filter through Perlite 476.

EXAMPLE 2

Preparation of Di-isocetyl Azelate

RAW MATERIALS

| | |
|---|---|
| Isocetyl Alcohol (Eutanol G-16) | 73.3% |
| Azelaic acid (Emerox 1144) | 26.5% |
| Hypophosphorous Acid, 50% | 0.1% |
| p-Toluenesulfonic Acid | 0.1% |

PROCEDURE

1. Charge the raw materials in the order listed above with agitation and nitrogen sparge.
2. Begin heating to 150° C. Water will begin to distill at 20° C.
3. Continue heating at 150° C. until the distillation of water is complete.
4. Sample each hour until the acid number is stable within 1.0 unit on two consecutive samples. The acid value should be below 4.0.
5. Cool to 100° C. and add 15% of the batch weight of an aqueous solution of sodium hydroxide equivalent to the acid value and 15% sodium sulfate with agitation.
6. Separate layers.
7. Dry the upper layer at 105° C. and 10 mm Hg with nitrogen sparge.
8. Filter through Perlite 476.

EXAMPLE 3

Preparation of Di-octyl/decyl Azelate

RAW MATERIALS

| | |
|---|---|
| Octyl/decyl Alcohol (C8–C10 Special) | 60.5% |
| Azelaic acid (Emerox 1144) | 39.3% |
| Hypophosphorous Acid, 504 | 0.1% |
| p-Toluenesulfonic Acid | 0.1% |

1. Charge the raw materials in the order listed above with agitation and nitrogen sparge.
2. Begin heating to 150° C. Water will begin to distill at 120° C.
3. Continue heating at 150° C. until the distillation of water is complete.
4. Sample each hour until the acid number is stable within 1.0 unit on two consecutive samples. If the acid number levels off at or above 5.0, it will be necessary to add enough octyl/decyl alcohol to complete the esterification.
5. Cool to 100° C. and add an amount of 50% sodium hydroxide equivalent to the catalyst and inhibitor.
6. Steam deodorize and dry at 105° C. and 10 mm Hg with nitrogen sparge.
7. Filter through Perlite 476.

Examples 1–3 were tested to determine their solubilities in various solvents, at room temperature. The results are listed in Table 1 below.

Samples of di-isocetyl azelate (3211–143), di-octyl/decyl azelate (3211–145), and isocetyl azelate (3211–139) were received and preliminary evaluations for application to skin care formulation were conducted.

Physical Observations:

Di-isoctyl azelate: Light yellow liquid at room temperature, moderate fatty odor, oily-lubricous skin feel with a highly emollient after feel, good spreading.

Di-octyl/decyl azelate: Pale yellow liquid at room temperature, very strong (unpleasant) share fatty odor, very dry application, somewhat raspy, dries quickly.

Isocetyl azelate: Yellow liquid with heavy precipitation at room temperature, clarifies at >80° C. with mixing, re-presicitates upon cooling to 65° C., moderate odor.

TABLE 1

SOLUBILITIES @ ROOM TEMPERATURE:

| SOLVENT | ISOCETYL AZELATE (CLARIFIED) | DI-ISOCETYL AZELATE | DI-OCTYL/ DECYL AELATE |
|---|---|---|---|
| water | insoluble | insoluble | insoluble |
| isopropanol | soluble | soluble | soluble |
| propylene glycol | vr. sl. sol. <0.1% | vr. sl. sol. <0.1% | vr. sl. sol. <0.1% |
| glycerine | insoluble | insoluble | insoluble |
| mineral oil (70sus) | Sol. >80° C. ppt <65° C. | soluble | soluble |
| myritol 318 | sol. >80° C. ppt <65° C. | soluble | soluble |
| IPM | soluble | soluble | soluble |
| IPP | soluble | soluble | soluble |
| G-16-OH | soluble | soluble | soluble |

Examples 1–3 were then evaluated to determine both their cloud and reclarification points. The results are listed in Table 2 below.

TABLE 2

CLOUD/RECLARIFICATION POINT:

| | | | |
|---|---|---|---|
| isocetyl azelate | 68° C./86° C. | 71° C./86° C. | 69° C./85° C. |
| di-isocetyl azelate | <0° C. | <0° C. | <−3° C. |
| di-octyl/decyl azelate | <−2° C. | <0° C. | <−3° C. |

Preliminary emulsification evaluation of isocetyl azelate:

A simple emulsion was prepared using TEA neutralized isocetylazelate as the sole emulsifier.

| | |
|---|---|
| carnation mineral oil | 20.00 |
| isocetyl azelate | 6.00 |
| deionized water | 71.80 |
| triethanolamine | 2.20 |
| | 100.00 |

Initially this system was a moderately thin, water-in-oil emulsion. The system separates at ≦24 hours at room temperature.

A second system was prepared increasing the level of isocetyl azelate and incorporating glyceayl monostearate as a co-emulsifier.

| | |
|---|---|
| carnation mineral oil | 20.00 |
| isocetyl azelate | 10.00 |
| emerest 2400 | 2.0 |
| deionized water | 64.4 |
| triethanolamine | 3.6 |
| | 100.00 |

This system is a white, fluid lotion of the water-in-oil type. Viscosity brookfield lvt. #3, GRPM, 25° C.=14000 CPS. It delivers a rolling application, and moderately fast drying, smooth afterfeel. The system is stable at room temperature >1 week.

The above system was repeated replacing isocetyl azelate with a "normal" ester, IPP. As expected, the system did not emulsify and separated immediately on cessation of mixing.

Isocetyl Azelate Saponification: (self emusificant)

An experiment was conducted in which isocetyl azelate was saponified, stoichiometrically, with triethanolamine. The molecular weight of isocetyl azelate was estimated to be 412, and it was assumed that one more of isocetyl azelate would react with one mole of triethanolamine. The equivalent weight of triethanolame 999 is reported as 150. Therefore if:

G16=Adzielate+TEA=TEA=G16-Azelate 1 mole≡1 mole

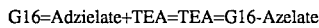 $\times \frac{1 \text{ mole triethanolamine}}{1 \text{ mole isocetyl azelate}} \times$ $\frac{150 \text{ sm triethanolamine}}{\text{mole triethanolamine}} = 0.3641$ gm of triethanolamine This was rounded off to 0.36 sm of triethanolamine.

| Test System: | % (w/w) |
|---|---|
| isocetyl azelate | 1.000 |
| deionized water | 98.64 |
| thiethanolamine-99 | 0.36 |
| | 100.00 |

The batch vessel was charged with water and isocetyl azelate and heated to 85° C. with mechanical mixing. Triethanolamine was added slowly, maintaining mixing and temperature. The system was allowed to mix, covered, for twenty minutes at 85° C. and then allowed to cool to room temperature, mixing throughout. Mixing was then stopped and observations were made.

1) isocetyl azelate was easily saponified with TEA at 85° C. forming a hazy "solution"
2) this hazy appearance maintained throughout cooling
3) at room temperature, and after the cessation of mixing, the system maintained its haze but several small "oil" droplets formed on the surface.
4) Based on the above observations, it is thought that saponified isocetyl azelate may be an interesting water-in-oil or mid-range HLB emulsifier.

Based on the above observations, it can be seen that saponified isocetyl azelate can be successfully used as a water-in-oil or mid-range HLB emulsifier.

Emulsification Evaluation Of Isocetyl Azelate

A simple emulsion was prepared using triethanolamine-neutralized isocetyl azelate as an emulsifier and glycerol monostearate as a co-emulsifier. The emulsion contained the following components:

| Component | Weight Percent |
|---|---|
| Carnation Mineral Oil | 20.00 |
| Isocetyl Azelate | 10.00 |
| Emerest 2400 | 2.00 |
| Deionized Water | 64.40 |
| Triethanolamine | 3.60 |

Observations:

This system appears as a white, fluid lotion of the water-in-oil type. The test system revealed a Brookfield viscosity LVT, #3, at 6 rpms and 25° C. of 14,000 cps. The test system appeared to have a rolling-type application and moderately fast drying-time with smooth skin after-feel. The system was stable at room temperature after more than a week.

Emulsification Evaluation of Di-isocetyl Azelate

An evaluation of di-isocetyl azelate in a simple oil-in-water emulsion was conducted. The emulsion contained the following components.

| Component | Weight Percent |
|---|---|
| Carnation Mineral Oil | 20.00 |
| Di-isocetyl Azelate | 10.00 |
| Emerest 2400 | 2.00 |
| Emersol 132 | 3.00 |
| Deionized Water | 57.50 |
| Propylene Glycol | 5.00 |
| Triethanolamine-99 | 3.60 |
| Germaben II | 1.00 |

*Emersol 132 = triple pressed stearic acid (approximately 45% stearic and 55% palmitic acids)
*Germaben II = preservative (mixture of methyl and propyl parabems along with diazolidinyl urea in a propylene glycol base)

| Type of Observation | Observation |
| --- | --- |
| (1) direct pH | 8.5 |
| (2) Brookfield Viscosity, LTV #3 at 6 rpm and 25° C. | 7900 cps |
| (3) Physical Appearance | white fluid |
| (4) Skin Feel | dry and smooth |

Emulsification Evaluation of Di-octyl/decyl Azelate

An evaluation of di-octyl/decyl azelate in a simple oil-in-water emulsion was conducted. The emulsion contained the following components.

| Component | Weight Percent |
| --- | --- |
| Carnation Mineral Oil | 20.00 |
| Di-octyl/decyl Azelate | 10.00 |
| Emerest 2400 | 2.00 |
| Emersol 132 | 3.00 |
| Deionized Water | 57.50 |
| Propylene Glycol | 5.00 |
| Triethanolamine-99 | 3.60 |
| Germaben II | 1.00 |

*Emersol 132 = triple pressed stearic acid (approximately 45% stearic and 55% palmitic acids)
*Germaben II = preservative (mixture of methyl and propyl parabems along with diazolidinyl urea in a propylene glycol base)

| Type of Observation | Observation |
| --- | --- |
| (1) direct pH | 8.6 |
| (2) Brookfield Viscosity, LTV #3 at 6 rpm and 25° C. | 6000 cps |
| (3) Physical Appearance | white fluid |
| (4) Skin Feel | dry |

What is claimed is:

1. A product of the process comprising reacting from about 40 to about 50 weight percent of azelaic acid with from about 50 to 60 weight percent of a C12–18 fatty alcohol, said product having the general formula I–IV:

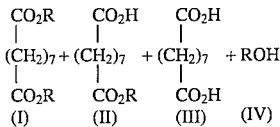

wherein R is a C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of said product.

2. The product of the process according to claim 1 wherein about 42 weight percent of azelaic acid are reacted with about 58 weight percent of a C12–18 fatty alcohol.

3. The product of the process according to claim 1 wherein said reaction is conducted in the presence of from about 0.15 to about 0.20 weight percent, based on the weight of said fatty alcohol, of a catalyst and a color inhibitor.

4. The product of the process according to claim 3 wherein said catalyst is a sulfonic acid.

5. The product of the process according to claim 1 wherein said C12–18 fatty alcohol comprises a Guerbet alcohol containing from about 12 to about 18 carbon atoms.

6. The product of the process according to claim 5 wherein said Guerbet alcohol is selected from the group consisting of isocetyl alcohol, 2-octyl dodecanol.

7. The product of the process according to claim 6 wherein said Guerbet alcohol is isocetyl alcohol.

8. The product of the process according to claim 1 wherein said reaction is conducted at a temperature in the range of from about 140° to about 160° C.

9. The product of the process according to claim 3 wherein said color inhibitor is hypophosphorous acid, 50%.

10. An aqueous composition comprising water and a self-emulsifying or emollient agent having the general formula I–IV:

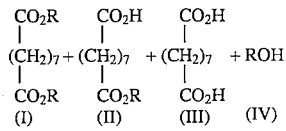

wherein R is a C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of said self-emulsifying or emollient agent.

11. The aqueous composition of claim 10 wherein from about 1 to about 25 weight percent, based on the weight of said composition, of said self-emulsifying or emollient agent is contained in said aqueous composition, with the remainder water.

12. The aqueous composition of claim 11 wherein said self-emulsifying or emollient agent is isocetyl azelate having the general formula I–IV:

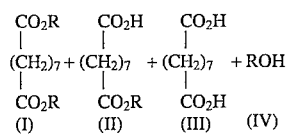

wherein R is a C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of said self-emulsifying or emollient agent.

13. The aqueous composition of claim 10 further comprising from about 0.1 to about 25 weight percent, based on the weight of said aqueous composition, of at least one active ingredient selected from the group consisting of a detergent, sunscreen, thickening agent, and mixtures thereof.

14. The aqueous composition of claim 13 wherein said active ingredient is a detergent.

15. The aqueous composition of claim 13 wherein said active ingredient is a sunscreen.

16. The aqueous composition of claim 13 wherein said active ingredient is a thickening agent.

17. A method of emulsifying or impeding emolliency to an aqueous composition comprising adding to said composition a self-emulsifying or emollient agent having the general formula I–IV:

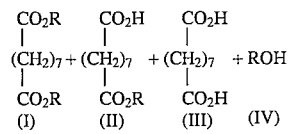

wherein R is a C12–18 alkyl group, and the product contains from about 40 to about 50 weight percent of (I), from about 50 to about 60 weight percent of (II) from about 1 to about 2 weight percent of (III), and from about 0 to about 1 weight percent of (IV), all weights being based on the weight of said self-emulsifying or emollient agent.

18. A method according to claim 17 wherein from about 1 to about 25 weight percent, based on the weight of said aqueous composition, of said self-emulsifying or emollient agent is added to said aqueous composition.

19. A method according to claim 18 wherein said self-emulsifying or emollient agent is isocetyl azelate having the general formula I–IV:

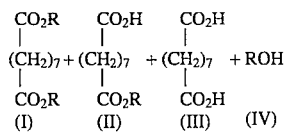

wherein R is a C12–18 alkyl group, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of said self-emulsifying or emollient agent.

20. A method according to claim 18 wherein R is isocetyl.

21. A composition comprising compounds having the general formula I–IV:

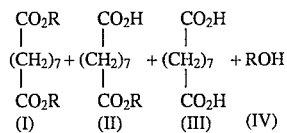

wherein R is a C12–18 alkyl group, and the composition contains from about 40 to about 50 weight percent of (I), from about 50 to about 60 weight percent of (II), from about 1 to about 2 weight percent of (III), and from about 0 to about 1 weight percent of (IV), all weights being based on the weight of said composition.

22. The composition of claim 21 wherein said composition comprises isocetyl azelate having the general formula I–IV:

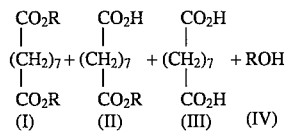

wherein R is isocetyl, and the product contains from about 40 to about 50 weight percent of (I), from about 50 to about 60 weight percent of (II), from about 1 to about 2 weight percent of (III), and from about 0 to about 1 weight percent of (IV), all weights being based on the weight of said composition.

* * * * *

UNITED STATES PATENT AND TRADEMARK OFFICE
CERTIFICATE OF CORRECTION

PATENT NO. : 5,578,642
DATED : Nov. 26, 1996
INVENTOR(S) : Barry A. Salka, Bruce W. Gesslein, Norman Milstein It is certified that error appears in the above-indentified patent and that said Letters Patent is hereby corrected as shown below:

In col. 9, line 20, "water-in-oil" should read --oil-in-water--.

In col. 9, line 25, "glyceayl" should read --glyceryl--.

In col. 9, line 35, "water-in-oil" should read --oil-in-water--.

In col. 9, line 49, "triethanolame 999" should read --triethanolamine 99%--.

In col. 9, line 51, "G16=Adzielate + TEA = TEA=G16-Azelate" should read --G16-Azelate + TEA → TEA-G16-Azelate--.

In col. 9, line 52, "1 mole ≡ 1 mole" should read --1 mole reacts with 1 mole--.

In col. 10, line 4, "thiethanolamine-99" should read --triethanolamine-99--.

In col. 10, lines 23-24, "water-in-oil" should read --oil-in-water--.

In col. 10, line 27, "water-in-oil" should read --oil-in-water--.

In col. 10, lines 42-43, "water-in-oil" should read --oil-in-water--.

Signed and Sealed this

Sixth Day of May, 1997

*Attest:*

BRUCE LEHMAN

*Attesting Officer*  *Commissioner of Patents and Trademarks*